United States Patent [19]

Cahn

[11] Patent Number: 5,008,116

[45] Date of Patent: Apr. 16, 1991

[54] IMMUNOSTIMULATORY MICROSPHERE

[76] Inventor: Frederick Cahn, 57 Raleigh Rd., Belmont, Mass. 02178

[21] Appl. No.: 270,276

[22] Filed: Nov. 14, 1988

[51] Int. Cl.⁵ .............................................. A61K 9/16
[52] U.S. Cl. .................................... 424/491; 424/87; 424/88; 424/407; 424/416; 424/426
[58] Field of Search .................. 424/491, 87, 88, 416, 424/426, 407

[56] References Cited

U.S. PATENT DOCUMENTS

| | | | |
|---|---|---|---|
| 4,225,581 | 9/1980 | Kreuter et al. | 424/88 |
| 4,350,629 | 9/1982 | Yannas et al. | 530/356 |
| 4,418,691 | 12/1983 | Yannas et al. | 623/15 |
| 4,505,266 | 3/1985 | Yannas et al. | 623/15 |

Primary Examiner—Merrell C. Cashion, Jr.
Assistant Examiner—P. L. Prater
Attorney, Agent, or Firm—Lieberman Rudolph & Nowak

[57] ABSTRACT

The invention relates to the use of an improved carrier or adjuvant to induce a therapeutic response to a weak antigen.

11 Claims, No Drawings

IMMUNOSTIMULATORY MICROSPHERE

BACKGROUND OF THE INVENTION

Vaccination or immunization is the most efficient measure to control infectious diseases in humans and in domestic animals. Also, in cancer immunotherapy, it is desired to stimulate an immune response against the tumor cells. Another application of immunization is in birth control. Sources of vaccine antigens include live attenuated or inactivated pathogens, and subunits, rDNA derived polypeptides, recombinant viruses, synthesized polypeptides and anti-idiotypes.

However, there are many diseases including AIDS and tropical diseases for which vaccines are not yet available or are not satisfactory. Similarly, immunotherapy is not a reliable method to treat tumors, in general.

Immunity to disease is due to the actions of specialized cells, especially the B and T lymphocytes. A basic description of the cellular basis of immunity may be found in *Molecular Biology of the Cell* (B. Alberts et al., Garland Publishing, Inc., New York, 1983). While the cellular basis of the immune system is understood in much greater detail than described in this reference, the basic principles can be clarified by its teachings, which state that the immune response is due primarily to the actions of specific cells, the B and T lymphocytes, which themselves consists of many subtypes. Virtually all lymphocyte responses are due to complex interactions among a variety of these and other cell types. In particular, the proliferation and differentiation of B and T cell effector cells and memory cells which underlies the desired objectives of immunization results from the interaction in the presence of the antigen between the class of T cells known as "Helper T cells" (Th) and either B lymphocytes or cytotoxic T cells. Also, the T cell recognition of antigens requires interaction with "antigen presenting cells" (APC) which incorporate antigen fragments into Type II MCH on the APC cell surfaces; APC cells include the B lymphocytes, macrophages, and the mast cells.

An addition, there are medical situations in which the suppression of immune reactions is desired; e.g., treatment of autoimmune diseases and allergies and in the transplantation of organs. In cellular terms, tolerance to antigen involves a class of T lymphocytes known as "Suppressor T cells" (Ts). The induction of immune tolerance is also within the scope of the instant invention.

This interaction between Th cells and other B or T cells is mediated by the production of hormonal factors known as lymphokines by Th cells which stimulate the growth and differentiation of effector and memory cells. The transmission of lymphokines from Th to target B or T cells is mediated by diffusion and takes place in the immediate vicinity of the Th-antibody interaction; sufficiently high concentrations of lymphokines to stimulate cell responses do not exist systemically. The interaction may also occur by synapse-like contacts between the cells. Monokines produced by the antigen presenting macrophages are also involved in the activation of T cells, representing another form immune cell communication by means of a soluble protein.

Generally, when killed organisms or their antigens are used for the vaccination or immunization the antigen is injected with a syringe into an appropriate body site. Thereafter, the T and B lymphocytes capable of recognizing the antigen may be attracted to the site of injection and interact with each other and with presenting cells such as mast cells there to produce the immune response. Alternatively, antigen can be transported in the lymphatic circulation to lymph nodes which are specialized organs which facilitate these cell-cell interactions with antigen.

Several problems occur in immunization, however. (1) the response is not always predictable: either immune stimulation or tolerance can be induced; (2) the response to a given antigen preparation in a given host species (e.g. human being, domestic animal, or laboratory animal) can vary greatly from individual to individual; (3) some antigens produce no response or weak responses in comparison to other antigens (4) the response may In particular, many highly purified bacterial and viral components are weak antigens. There is a particular need to overcome this problem since advances in molecular biology can now make available small and highly purified antigenic components of pathogenic organisms.

Two methods are used to partially overcome the above described problems: carriers and adjuvants. These methods are not always clearly distinguished, and the instant invention contains elements of both of these. A carrier is generally a macromolecule to which a hapten (an antigenic determinant which binds to lymphocyte receptor but cannot induce an immune response) is bound; carriers include tetanus toxoid, diphtheria toxoid and purified protein derivatives. An adjuvant enhances an immune response; examples are Freund's adjuvant (used in animal experimentation), and alum (sometimes used in human vaccines). Other adjuvants include SAF-1 (Synthex), Nor-MDP (Ciba-Geigy), Sqaulene, and Zymozan and "iscoms" (immune-stimulating complex). Additional information on adjuvants included within the scope of this invention are found in Adam, *Synthetic Adjuvants,* Wiley & Sons, 1985.

Novel concepts in adjuvants or improved antibody presentation include the use of lymphokines as adjuvants, the coupling of antigens with antibodies against the surface molecules of antigen presenting cells (e.g. Type II major histocompatibility complex (MHC); B cell surface antibody). Another recent advance in antigen presentation is the use of biodegradable microspheres made of polylactic/polyglycolic acid copolymers to prolong antibody release. These approaches are disclosed in the "Report of a Meeting on Basic Vaccinology" held by the WHO in Geneva, Dec. 8–11, 1987. Similar approaches are disclosed in U.S. Pat. Nos. 4,225,581 and 4,269,821.

It has been suggested that porous collagen-glycosaminoglycan (collagen-GAG) can be used as a microsphere carrier for the controlled release of antigen or attenuated microorganisms. The porous collagen-GAG can be used to immobilize microorganisms in the pores by physical entrapment or chemical crosslinking; other antigens can be chemically crosslinked to the porous matrix. These microspheres can thus be used as biodegradable vehicles for the antigens. A possible disadvantage of collagen as a material to form microspheres in comparison with certain synthetic materials such as polylactic acid/polyglycolic acid copolymers is the endogenous antigenicity of collagen. Such macroporous microspheres may range from 1 $\mu$m to about 1000 $\mu$m. A preferred particle size for such a microsphere would be less than about 50 $\mu$m to enable the adjuvant to be delivered by injection. For introduction of microorganisms into a preformed microsphere, a desired pore size would be in the micron range; for immobilization of molecular antigens, submicron pore sizes would be appropriate.

A similar controlled release experimental vaccine for rabbits has made by co-polymerizing virus particle and virus subunits into rabbit serum albumin beads (Martin, M.E. et al., *Vaccine*, 1988 February 6(1). p 33–8).

For induction of tolerance, experiments are underway in which microspheres of porous collagen-chondroitin-6-sulfate (C6S) (obtained from Biomat Corporation) of about 500 μm diameter and with mean pore sized of about 20 m near the surface and of about 50–80 μm in the interior are seeded with bone marrow cells from a donor animal. These microspheres are implanted into a host animal, which is also treated with an antilymphocyte serum. This process is intended to induce tolerance in the host so that an organ can also be transplanted from that donor to that host without rejection by the host animal. This procedure can be distinguished from the application of the instant invention in the induction of tolerance as its sole application to organ transplantations and in its specific use of bone marrow cells as well as antilymphocyte serum. Also, the antigens are not crosslinked to the collagen-GAG matrix.

Biodegradable microspheres can help in the presentation of antigen, for example by prolonging delivery, but they do not enhance or direct the cellular interactions underlying immune response, which is an objective of this invention.

OBJECTIVES OF THE INVENTION

One object of the instant invention is to bring about the efficient interaction of lymphocyte cell types resulting in a stronger, longer lasting, or more consistent immune response.

A further object of the invention is to target the interaction with antigen to specific classes of cells so as to preferentially stimulate either humoral antibody response, cytotoxic T cell response, or immune tolerance.

Another object of the invention is to induce a therapeutic response to a weak antigen by providing an improved carrier or adjuvant for the antigen.

Another object of the invention is to prolong the contact of antibody and lymphocytes by providing a slow release mechanism for the antigen.

Another object is to provide an improved adjuvant by incorporating natural lymphokines in a controlled release form together with the carrier and antigen.

Another object is to enhance the cellular immune attack on pathogens such as viruses by trapping pathogens or pathogeninfected cells, thus controlling the presentation of the pathogens to the cellular immune system or enhancing the delivery of chemotherapeutic agents. These and other objectives will be apparant from the description below.

SUMMARY

A macroporous microsphere is disclosed comprising a particle mode of a polymer, having a size of 1 to 1000 microns, with pores having a mean pore diameter of 0.1 to 100 microns. The microsphere pores may be adapted to bind to a hapten.

DESCRIPTION OF THE INVENTION

The basic invention includes a macroporous microsphere or other particulate shape having a high internal surface area. Antigens are physically entrapped in or chemically crosslinked to the interior. The microsphere can be made from natural biopolymers, such as collagens or glycosaminoglycans (GAG) or from synthetic polymers such as polylactic acid polyglycolic acid copolymer. Ideally, the particle is sufficiently small that it can be injected with a syringe, e.g., 1 to 100 μm preferably below about 50 μm diameter. The open pore structure has a mean pore size such that various classes of lymphocytes can enter and interact both with antigen and with each other. (Since small lymphocytes have diameters of about 6 μm, activated T cells have diameters of about 9 μm, and activated B cells have diameters of about 8–12 μm, mean pore sizes of about 5–15 μm would be optimal, although acceptable pore sizes could range from about 3–100 μm.)

Microspheres fitting these specifications can be formed from the collagen-GAG copolymers developed by Yannas and described in U.S. Pat. Nos. 4,060,081, 4,280,954, 4,350,629, 4,418,691, 4,448,718, 4,458,678, 4,522,753, 4,405,266. Other similar materials which may be suitable are described in U.S. Pat. Nos. 4,614,794 and 4,378,017.

Other materials which could be used to form microspheres include carbohydrate polymers such as those under development by Alpha-Beta Technology (Worcester, Mass.) and surface-active synthetic copolymers such as those under development by CytRx (Norcross, Ga.). Any polymeric adjuvant material may be used to construct the porous matrix, or any of these agents may be crosslinked to it; polymeric adjuvants include glucans, polysaccharides, lipoproteins, poly (CTTH-iminocarbonate) [Kohn, J. et al, J. Immunol. methods, 95:31–8, 1986], ethylene-vinyl acetate copolymer [Niemi, S. M., et al, Lab. Anim. Sci. 35:609–12, 1985], etc. Preferably, all materials used herein should be biodegradable.

Larger particles, such as particles usable as porous microcarriers in animal cell culture with particle sizes of 300–1000 m are used also, but are not as easily deliverable by syringe. Other forms of macroporous materials such as sheets, are within the scope of this invention, but are also not easily injectable by syringe.

Antigens which can be crosslinked to such a particle include whole inactivated pathogens, and subunit thereof, rDNA derived polypeptides, recombinant viruses, synthesized polypeptides and anti-idiotypes. Whole microorganisms or animal cells can be also physically entrapped in small pores and cul-de-sacs of the matrix without necessarily being crosslinked to it. Procedures to entrap whole cells in porous matrices are described in U.S. Pat. Nos. 4,418,691, 4,458,678, and 4,505,266 to Yannas, et al.

Suitable chemical crosslinking procedures for immobilization of the antigens include bifunctional aldehydes such as glutaraldehyde, carbodiimides, and other "linkers" or crosslinking agents well known in the art of the immobilization of antibodies, other proteins, or carbohydrates. If the microsphere is made primarily of collagen, and it is desirable to avoid altering the antigenic properties of the collagen, the crosslinking method of Siegel (U.S. Pat. No. 4,544,638) may be used. In the preferred mode of using the invention, an inert insoluble microsphere is preformed and the antigen is contacted with it and crosslinked to it later, followed by washing out the unreacted components, and formulating the microspheres into an injectable form. A crosslinking method which contains separate steps of activation of the matrix, for example with cyanogen bromide, followed by reaction of the antigen with the activated matrix may be preferred in this case since it offers less risk of altering the antigenic properties of the antigen.

A particle which maintains the lymphocytes in the interior in contact with the antigen has basic steric or geometric advantages over a particle which releases antigen to interact with lymphocytes exterior to it:

1. By immobilizing antigens on the large surface area, locally high antigen concentrations can be maintained in direct proximity to or direct contact with the lymphocytes.
2. Given that the clonal selection theory predicts that a fixed number of lymphocytes reactive to a given antibody are available to be recruited to the vicinity of the antigen injection, internalizing them in the porous particle creates a higher concentration of these cells, thus increasing the probability of forming the cell-cell contacts important for immune stimulation.
3. Lymphokine and monokine concentrations are determined by a balance between production by the cells and diffusion from their vicinity. A higher concentration of Th cells will increase the concentration of lymphokines in the vicinity of the receptor cells because the higher cell concentration and smaller surface area of the region in which the interacting cells are located.
4. The high surface area matrix also can serve as a carrier to enhance the response to the bound antigen or hapten.
5. It may be possible to control the porosity of the material to physically exclude certain classes of lymphocytes.

Although synthetic polymers or natural biopolymers such as collagen can be used to form the matrix of the microsphere, collagen-GAG has certain advantages:

1. Collagen and GAG are natural polymers which have low toxicity and are naturally biodegradable. The degradation rate can be controlled by variation of GAG concentration and degree of crosslinking. Ideally, the degradation rate is designed to allow sufficient time for desired immune responses to occur, but permit rapid degradation thereafter.
2. Collagen-GAG has much lower immunogenicity in comparison with native collagen. In artificial skin wound dressings, the dressing is accepted by the host even though bovine collagen is used. Immunogenicity may be further reduced by use of collagen of human origin (e.g. Residue B of Play et al, U.S. Pat. No. 4,511,653) or the use of a teliopeptide collagen in which the more immunogenic teliopeptide regions of the collagen molecules are removed.
3. Collagen-GAG is highly compatible with blood in comparison to native collagen.
4. The GAG component of crosslinked collagen-GAG materials can be varied to modify the biological properties of the complex.

Other polyanionic polysaccharides, such dextran sulfate and those of marine plant origin (carrageenans, alginates), can be substituted for GAG in the production of porous matrices; for example, U.S. Pat. No. 4,614,794 describes such a modification. Since in in vitro experiments, such anionic polysaccharides exhibit some of the biological properties of the GAGs (Fujita et al, Hepatoloqy, Vol. 7, p 1S-9S, 1987), matrices formed from all of these materials are considered within the scope of this invention.

U.S. Pat. No. 4,378,017 describes composite materials of collagen and de-N-acetylated chitin. The use of such materials to form the microspheres of this invention are also within the scope of this invention. Crosslinked gels of hyaluronic acid (U.S. Pat. No. 4,636,524), other GAGs, or polyanionic polysaccharides may also be suitable materials if formed into porous microspheres.

The basic invention also includes certain elaborations to enhance or control the immune response or to increase the ease of its administration.

1. In addition to antigen, small particles of a controlled release formulation of lymphokines and/or monokines can be incorporated into the matrix.
2. Antibodies against MHC II or B cell surface antibodies can be crosslinked to the matrix in addition to antigen.
3. The matrix can be preseeded with host lymphocytes or with presenting cells, such as mast cells.
4. To improve the ease of injecting the microspheres through a syringe, the particles can be prepared in a compressed form, and allowed to expand after injection. A specific prototype method of achieving such a compression is presented in Example 2, below.
5. The microspheres can be injected together with other adjuvants, such as alum, or iscoms.
6. Inflammatory or immunostimulatory agents such as histamine or prostaglandins can be incorporated, preferably as a controlled release formulation; diffusion of these agents into surrounding tissues can help recruit lymphocytes to the microsphere.
7. Presenting the antigen in the interior of microspheres offers unique options in constructing polyvalent vaccines; Two or more antigens can be combined into the same particle to enhance mutual recognition of the antigens, or two or more antigens can be presented on separate particles to stimulate independent cellular responses to these antigens.
8. Other biodegradable fibers can be incorporated into the matrix to enhance mechanical strength.
9 Destruction of lymphocytes responding to the antigen-containing microsphere can be accomplished by the administration of cytotoxic agents, such as antilymphocyte serum or anti-metabolites such as cyclophosphamide. Controlled release formulations of these cytotoxic agents can be incorporated into the microspheres. Either immune tolerance (by destruction of responding B cells or cytotoxic T cells) or the reversal of tolerance (by destruction of suppressor T cells) could be accomplished in this way. The targeting of the response to cytotoxic or suppressor cells might be accomplished by the method described below.

In addition to these elaborations, an important objective of the instant invention is the ability to design the microsphere so as to more accurately target the immune response. This possibility arises from the role of extracellular matrix (ECM) molecules in the growth and differentiation of cells. The immune response may be regarded as a specific and specialized case of cell differentiation. Co-pending U.S. patent application No. 07/149,651 describes the formation of materials from components of the ECM, including collagen-GAG materials and "biomatrix" (an extract of the ECM) designed to support the differentiation of specific cells or to maintain their differentiation in vitro; this application is incorporated herein by reference.

To direct specific lymphocyte cell types to the matrix, specific collagen and GAG components attractive to these cells can be incorporated into the matrix. Different regions of the lymph node are attractive to the T and B lymphocytes; presumably this attraction is mediated by differences in the chemical composition of the extracellular matrix of these regions. Although this chemistry is not yet known in detail, the lymph nodes are rich in "reticular fibers" comprised of type III collagen fibers as well as type IV collagen and heparan sulfate proteoglycans. Other evidence for the importance of ECM components to immune responses are the observations that both heparin proteoglycans and chondritin sulfate proteoglycans are associated with the mast cells and natural killer cells which are associated with inflammatory responses (Stevens, R. L., Ciba-Found-Symp. 1986, p 272-85). Additional evidence for the importance of the GAG component of the ECM in immune responses comes from observation that a chondroitin sulfate proteoglycan is associated with the immunoregulatory Ia proteins of the MHC; inhibitors that prevent the addition of the GAG apparently depress the antigen-presenting function of the MHC.

Accordingly, one embodiment of this invention is the construction of the collagen-GAG matrix from specific collagens and GAGs chosen empirically to increase the concentrations within the matrix of specific subtypes of lymphocytes, especially specific regulatory T lymphocytes. By increasing Th concentration, the immune response to antigen would be enhanced, by increasing Ts, tolerance may be enhanced. Similarly, increasing concentrations of cytotoxic T cells relative to B cells would enhance the cellmediated immunity, whereas the increase in B cells would favor humoral antibody responce.

In addition to vaccine applications of porous microspheres, the treatment of AIDS or infection by its cause, the human immunodeficiency virus (HIV) by stimulation of the CD8+subset of suppressor T cells, as proposed by Levy et al (Science, Vol 234, p1563-6, 1986), is another application; such an approach would be advantageous in comparison to the isolation and in vitro replication of the CD8 subset. Either HIV antigens, T cell growth factors (preferably in controlled release form), or both could be incorporated into the microsphere to target activity of the microsphere to the desired cell subclass.

As another therapeutic use, the porous microspheres described herein can be utilized as traps for pathogens. One example is a porous particle which selectively traps virus-infected cells, for example HIV-virus infected T lymphocytes. Since HIV-virus infected cells express the gp120 antigen on their surfaces, a matrix crosslinked to gp120 antibodies, or to soluble CD4 would bind infected cells. Cytotoxic agents in immobilized or controlled release form could also be incorporated to kill the infected cells. Alternatively, antiviral agents such as azidothymidine (AZT), dextran sulfate, ddC, ddA, ddI, phosphonoformate, rifabutin, ribaviran, phosphorothionate oligodeoxynucleotides, castanospermine, alpha interferon, or ampligen could be incorporated. These agents and their utilization in AIDS therapy are described by Yarchoan et al (*Scientific American*, October, 1988, p 110). Other anti-AIDS drugs used in experimental therapy, such as AL721, azimexon, cyclosporin, foscarnet, HPA-23, imreg-1, inosine pranobex, D-penicillamine, and suramin, could also be used; these agents are described in *Chemical & Enqineerinq News*, December 8, 1986, p 7-14. If a collagen matrix is used, dextran sulfate can be incorporated in place of or in addition to GAG, using fabrication and crosslinking methods. Diffusible chemoattractive agents in controlled release form might also be included to enhance the recruitment of the infected T cells. By use of pore sizes too small for fibroblasts to easily enter, the selectivity of the matrix for lymphocytes is enhanced.

Other possible applications of porous cytotoxic traps designed on these principles would include treatments for leukemias and autoimmune disease. For autoimmune disease treatment, either an anti-idiotype antibody or the cellular molecule being attacked by the autoimmune disease (either extracted from tissue or made by recombinant DNA technology) is crosslinked to the matrix. Leukemia cells may be attracted by choice of extracellular matrix components and/or by crosslinked antibodies or anti-idiotypes. Once attracted to the matrix, the cells can be either killed by cytotoxic agents or induced to differentiate by differentiation factors.

Still another application of the porous microsphere described herein is to entrap pathogenic parasites, bacteria, yeast, virus, etc. by means of antibody to the pathogen crosslinked to the matrix. Affinity for the pathogen is accomplished by use of a cellular macromolecule recognized by the pathogen, for example soluble CD4 to entrap HIV virus. Such as system functions to kill the pathogen by use of cytotoxic agents or antibiotics in high local concentrations, or improves the presentation of the pathogen to the immune system. For example, as an AIDS therapy, immobilizing the virus in this way inhibits the formation of syncytia and thus attenuates the virulence of the virus. For these applications, the pore size of the matrix can be decreased to below 5 $\mu$m to prevent entry of lymphocytes and thus inhibit direct interaction of the pathogen with host cells, but allow the entry of viruses or macromolecules. To allow entry of HIV virus, with a diameter of about 0.13 $\mu$m, the mean pore size should be greater than about 0.1 $\mu$m. Optimal mean pore sizes would be between about 0.2 $\mu$m and 2 $\mu$m. In the case of entrapped HIV virus, the infection of lymphocytes during the biodegradation of the matrix may be controlled by incorporation into the matrix of some of the antiviral agents listed above. Particles with pore sizes below about 1 $\mu$m could be made with diameters smaller than about 10 $\mu$m; such particles could be injected into the blood stream, if made of blood compatible biomaterials. A collagen-GAG matrix including heparin as part or all of the GAG would have good blood compatibility.

EXAMPLES

Example 1

Bovine hide collagen from limed hides is dispersed in 900 ml of 0.05M acetic acid at 0.55 % w/v and comminuted with an IKA T50 blender for about 5 minutes until a viscous gel is formed; 100 ml of 0.4 % w/v C6S is added slowly while blending is continued. The mixture is degassed, and formed into droplets about 50 $\mu$m in diameter. The droplets are frozen at a rate such as to obtain mean pore sizes of about 10 $\mu$m, freeze dried, and dehydrothermally crosslinked by heating to 105° C. for 24 hours in a vacuum oven. The particle is rehydrated in 0.05M acetic acid (or in phosphate buffered saline) and mixed with tetanus toxoid antigen at 1-100 $\mu$/ml.

Glutaraldehyde (0.25 % final) is added and the mixture is incubated at room temperature for 24 hours. The particles are washed in sterile saline for injection.

Example 2

Human placental collagen, residue B of Play et al (U.S. Pat. No. 4,511,653) is substituted for the bovine hide collagen, in the procedure of Example 1.

Example 3

Insoluble comminuted collagen rich in types III and IV is extracted from bovine lung or kidney, and extracted with 0.05M sodium hydroxide. This collagen is used in place of hide collagen in example 1.

Example 4

Heparin, extracted from intestinal mucosa, is substituted for the C6S in examples 1, 2 or 3.

Example 5

A sheet of freeze dried, dehydrothermally crosslinked porous collagen-GAG is prepared by methods of Yannas with a thickness of 50 μm and a mean pore size of 10 μm. The sheet is rehydrated, tetanus toxoid antigen at 1-100 g/ml is added and the complex is crosslinked with glutaraldehyde as in Example 1. After washing with phosphate buffered saline (PBS), the material is maintained at about 37° C. and 1-5 % w/v agarose with a melting point of about 30°-35° C. is added. The sheet is compressed between absorbent layers to about ⅓ of its original thickness, and is removed from the blotters and chilled to gel the agarose, The material is comminuted to particles of about 17 μm mean diameter, and suspended in chilled saline for injection. The material can be warmed to about 25° C. before injection.

All references named herein are incorporated by reference. While certain preferred embodiments of the invention are disclosed herein, numerous alternative embodiments are contemplated as falling within the scope of the invention. Consequently, this invention is not limited to the specific teachings herein.

Based upon the examples above, the invention described herein is useful for the formulation of vaccines with improved adjuvant activity, targeting an immune response to an antigen and targeting chemical compounds to specific cells or pathogens.

I claim:

1. A macroporous microsphere comprising a particle and an antigenic component, selected from the group consisting of whole inactivated pathogens and submits thereof, RDNA derived polyreptides, recombinant viruses, synthesized polypeptides and anti-idiotypes, and whole microorganisms or animal cells wherein said antigenic component is physically entrapped in or chemically crosslinked, to the interior of said particle, said particle being comprised of a polymer, and said microsphere having size of 1 to 1000 μm, and pores with a mean pore diameter of 0.1 to 100 μm.

2. The microsphere of claim 1 wherein said antigenic component is a hapten.

3. The microsphere of claim 1 wherein said polymer is selected from the group consisting of a biopolymer, synthetic polymer, carbohydrate, protein, lipoprotein, surface active synthetic copolymer, and polysaccharide.

4. The microsphere of claim 3 wherein the biopolymer is a collagen.

5. The microsphere of claim 4 wherein the bipolymer is a collagen-glycosaminoglycan copolymer.

6. The microsphere of claim 3 wherein the synthetic polymer is a polylactic acid/polyglycolic acid copolymer.

7. The microsphere of claim 3 wherein the polymer is a collagen chondroitin-6-sulfate copolymer.

8. The microsphere of claim 3 wherein the polymer is a collagen and de-N-acetylated chitin.

9. The microsphere of claim 5 wherein the polymer further contains hyaluronic acid.

10. A microporous microsphere as defined in claim 1 wherein the particles are compressed.

11. A microporous microsphere as defined in claim 1 further containing an MHC II antibody.

* * * * *

UNITED STATES PATENT AND TRADEMARK OFFICE
CERTIFICATE OF CORRECTION

PATENT NO. : 5,008,116
DATED : 4/16/91
INVENTOR(S) : Frederick Cahn

It is certified that error appears in the above-identified patent and that said Letters Patent is hereby corrected as shown below:

Column 2, line 15: after "may" insert -- not be maintained for a sufficiently long time -- .

Column 3, line 53: change "pathogeninfected" to -- pathogen infected -- .

Column 4, line 45: change "subunit" to -- subunits -- .

Column 7, line 35: change "cellmediated" to -- cell mediated -- .

Col. 10

Amend claim 1 to read as follows:

-- 1. (amended) A macroporous microsphere comprising a particle and an antigenic component selected from the group consisting of whole inactivated pathogens and [submits] subunits thereof, [RDNA] r DNA derived [polyreptides] polypeptides, recombinant viruses, synthesized polypeptides and antiidiotypes, and whole microorganisms or animal cells, wherein said antigenic component is physically entrapped in or chemically crosslinked [,] to the interior of said particle, said particle being composed of a polymer, and said microsphere having a size of 1 to 1000 µm, and pores with a mean pore diameter of 0.1 µm to 100 µm. -- .

Signed and Sealed this

Twenty-second Day of December, 1992

Attest:

DOUGLAS B. COMER

Attesting Officer   Acting Commissioner of Patents and Trademarks